United States Patent
Iseki et al.

(10) Patent No.: US 8,487,282 B2
(45) Date of Patent: Jul. 16, 2013

(54) PARTICLE BEAM IRRADIATION APPARATUS AND CONTROL METHOD OF THE PARTICLE BEAM IRRADIATION APPARATUS

(75) Inventors: Yasushi Iseki, Yokohama (JP); Katsushi Hanawa, Kita-Ku (JP); Kazunao Maeda, Suginami-Ku (JP); Nobukazu Kakutani, Yokohama (JP); Takuji Furukawa, Chiba (JP); Taku Inaniwa, Chiba (JP); Shinji Sato, Chiba (JP); Kouji Noda, Chiba (JP)

(73) Assignees: Kabushiki Kaisha Toshiba, Tokyo (JP); National Institute of Radiological Sciences, Chiba-Shi (JP)

( * ) Notice: Subject to any disclaimer, the term of this patent is extended or adjusted under 35 U.S.C. 154(b) by 0 days.

(21) Appl. No.: 13/577,509

(22) PCT Filed: Feb. 7, 2011

(86) PCT No.: PCT/JP2011/052523
§ 371 (c)(1),
(2), (4) Date: Aug. 7, 2012

(87) PCT Pub. No.: WO2011/099449
PCT Pub. Date: Aug. 18, 2011

(65) Prior Publication Data
US 2012/0305796 A1    Dec. 6, 2012

(30) Foreign Application Priority Data
Feb. 10, 2010    (JP) ................... 2010-028047

(51) Int. Cl.
*A61N 5/10*    (2006.01)
(52) U.S. Cl.
CPC ........................................ *A61N 5/10* (2013.01)
USPC ....................................... 250/492.3; 250/397

(58) Field of Classification Search
USPC ............................................. 250/492.3, 397
See application file for complete search history.

(56) References Cited

U.S. PATENT DOCUMENTS
7,838,855 B2 *   11/2010   Fujii et al. .................. 250/505.1

FOREIGN PATENT DOCUMENTS
| JP | 3 108687 | 5/1991 |
| JP | 2002 6051 | 1/2002 |
| JP | 2008 175829 | 7/2008 |
| JP | 2009 66106 | 4/2009 |
| JP | 2010 12056 | 1/2010 |

OTHER PUBLICATIONS

Internatiional Preliminary Report on Patentability Issued Sep. 18, 2012 in PCT/JP11/52523 Filed Feb. 7, 2011.
International Search Report Issued Mar. 15, 2011 in PCT/JP11/52523 Filed Feb. 7, 2011.

* cited by examiner

*Primary Examiner* — Kiet T Nguyen
(74) *Attorney, Agent, or Firm* — Oblon, Spivak, McClelland, Maier & Neustadt, L.L.P.

(57) ABSTRACT

A particle beam irradiation apparatus that can measure and display a dose two-dimensional distribution during scan while reducing degradation of a particle beam shape, including a particle beam generation portion; a particle beam emission control portion; a two-dimensional beam scanning portion; a sensor portion including first linear electrodes arranged in parallel in a first direction and second linear electrodes arranged in parallel in a second direction orthogonal to the first direction; a beam shape calculation portion that calculates a center of gravity of the particle beam from outputs of each the first linear and second linear electrodes and that obtains a two-dimensional beam shape of the particle beam around the center of gravity; a storage portion that accumulates and stores the two-dimensional beam shapes; and a display portion that displays the two-dimensional beam shapes as a two-dimensional distribution of a dose.

12 Claims, 13 Drawing Sheets

PARTICLE BEAM IRRADIATION APPARATUS AND CONTROL METHOD OF THE PARTICLE BEAM IRRADIATION APPARATUS

TECHNICAL FIELD

The present invention relates to a particle beam irradiation apparatus and a control method of the particle beam irradiation apparatus, and particularly for directing a heavy particle beam of carbon, a proton beam, or the like to an affected area to treat cancer.

BACKGROUND ART

In Japan today, cancer is the highest cause of death, and more than 300,000 domestic people die of cancer every year. Under the circumstances, a particle radiation therapy using a carbon beam and a proton beam with excellent features of high therapeutic effects and few side effects is drawing attention. In the therapy, a particle beam emitted from an accelerator can be directed to cancer cells to destroy the cancer cells while reducing influence on normal cells.

In the therapeutic method, a currently used particle beam irradiation method is a method called a broad beam method. In the broad beam method, a diameter of the particle beam is expanded to a size greater than the affected area based on a method called a wobbler method or a double scatter method. A multi-leaf collimator formed by a large number of metallic plates (leaves) limits an irradiation area to direct the beam in accordance with a shape of the affected area. A beam range expansion apparatus called a ridge filter expands the beam in a beam travelling direction (beam axis direction). A polyethylene beam range shaping apparatus called a compensator adjusts a beam termination position according to a shape (outline) of the affected area at a deep position to direct the beam.

However, the broad beam method is not capable of precise three-dimensional adjustment of the beam in accordance with the shape of the affected area, and there is a limit to reducing the influence on the normal cells around the affected area. The geometric collimator and the compensator are created for each affected area (and for each irradiation direction relative to the affected area), and there is a problem that radioactive wastes are generated after therapeutic irradiation.

Consequently, scanning irradiation for dividing the affected area inside of a body into three-dimensional lattices before irradiation is being developed as a further advanced form of irradiation in the particle beam treatment. In the scanning irradiation, the beam can be accurately adjusted to the affected area in the beam axis direction without using the geometric collimator or the compensator, and exposure to the normal cells can be reduced compared to conventional two-dimensional irradiation.

For example, each point is irradiated as follows in three-dimensional irradiation called spot scanning irradiation.

When a predetermined dose is directed to a point (operation of determining the irradiation dose for each irradiation point is called treatment planning), a scanning control apparatus receives a completion signal from a dose monitor and outputs a spot switch command. A beam emission control apparatus terminates beam emission based on the spot switch command. At the same time, an electromagnet power supply that provides an exciting current to a scanning electromagnet that scans the particle beam starts setting a current value corresponding to coordinates of a next irradiation point. When receiving a completion signal of the current value setting of the electromagnetic power supply, the scanning irradiation apparatus outputs a beam start command to the beam emission control apparatus, and irradiation for the next point is started. This is sequentially repeated to irradiate a treatment region with respect to one irradiation slice. When the irradiation is finished, the beam emission is temporarily terminated. Energy of the beam emitted from the accelerator is changed, or a range adjustment apparatus called a range shifter is controlled to change a beam termination position (slice) in the beam travelling direction. In this way, the scanning irradiation and the slice switch are sequentially performed for irradiation of the entire treatment region.

A weak point of the spot scanning irradiation is that the beam emission cannot be actually immediately terminated even if the beam emission control apparatus outputs the beam termination command. Therefore, a leakage dose is directed to the affected area when an exciting current of the electromagnet is changed, i.e. when the irradiation position is moved. This is particularly a problem when the irradiation dose (set dose) for each point is small, because a ratio of the leakage dose (leakage dose/set dose) is large. To prevent the problem, beam intensity needs to be reduced to make the ratio of the leakage dose relatively small. However, the reduction in the beam intensity leads to an increase in the time for treatment, and a physical burden of the patient increases.

A method called a raster scanning method is newly developed to solve the problem that the beam intensity cannot be increased in the spot scanning method (see Non-Patent Document 1 or the like). In the method, the beam is not terminated when the irradiation point is moved, unlike in the spot scanning method. Therefore, the beam is irradiated when the particle beam moves between a termination irradiation position (a point for directing a dose that is set when the particle beam is terminated, not when the particle beam is moving, will be called a termination irradiation point) and a termination irradiation point. The treatment planning including an amount of irradiation during the irradiation, i.e. irradiation dose at each termination point, is optimized.

In the scanning irradiation, an irradiation port includes a position monitor to ensure that the beam is directed to a correct position. If there is a difference between a predetermined irradiation position and a position measured by the position monitor due to a current setting abnormality of the scanning electromagnet power supply or due to displacement in the beam position at a beam transport section from an upstream accelerator to a scanning apparatus, a position monitoring mechanism (called "position monitoring controller" here) in the scanning control apparatus outputs an interlock signal, and the therapeutic irradiation is temporarily suspended.

An example of the position monitor for scanning irradiation is disclosed in, for example, Patent Document 1. In the position monitor, for example, an electrode section of accumulated electrodes of an ionization chamber is divided into a large number of electrically non-contact strips in one axial direction, and a measurement circuit is connected to each strip. The measurement circuit includes an integration portion that stores, for each irradiation spot, electricity equivalent to charge accumulated on the strip. Voltages output from the integration portions are extracted as digital signals by A/D converters (hereinafter, described as "ADC circuits"). Computation, such as calculation of a center of gravity, is applied to the digital signals to calculate spot positions.

CITATION LIST

Patent Document

Patent Document 1: Japanese Patent Laid-Open No. 2001-33560

Non-Patent Document

Non-Patent Document 1: Takuji Furukawa and eight others, "Design Study of Three-Dimensional Scanning Irradiation Apparatus", National Institute of Radiological Sciences HIMAC Report: HIMAC-124, issued by National Institute of Radiological Sciences, April 2007.

SUMMARY OF INVENTION

Technical Problems

Meanwhile, there is a strong demand from doctors and radiological technicians for visually checking dose profiles of slices during irradiation, i.e. visually checking whether a dose two-dimensional distribution during scan is a correct distribution. The position monitor is configured to check whether the position is correct at each irradiation point and is not configured to output dose profiles as a two-dimensional distribution.

An example of an apparatus that measures the dose profiles includes an apparatus called a multi-array profile monitor including signal electrodes of a parallel plate ionization chamber formed in a multi-array. However, signal lines need to be extracted from each array in the apparatus, and the signal electrodes become thick. In the scanning irradiation, a beam size (beam width) is an important parameter in forming an excellent dose distribution. However, if an apparatus (multi-array profile monitor) with thick electrodes is arranged on a path of the particle beam, the beam is scattered, and the beam size (beam width) is extended to an unallowable range. An increase in the beam size results in a dose distribution with a blurred irradiation area. Highly accurate irradiation corresponding to the shape of the affected area cannot be performed, and normal tissues outside of the affected area are more exposed to radiation.

The present invention has been made in view of the circumstances, and an object of the present invention is to provide a particle beam irradiation apparatus and a control method of the particle beam irradiation apparatus that can measure and display a dose two-dimensional distribution during scan with a simple configuration, while reducing degradation of a particle beam shape.

Solution to Problem

To solve the problems, the present invention provides a particle beam irradiation apparatus comprising: a beam generation portion that generates a particle beam; a beam emission control portion that controls emission of the particle beam; a beam scanning portion that two-dimensionally scans the particle beam; a sensor portion including a plurality of first linear electrodes arranged in parallel in a first direction and a plurality of second linear electrodes arranged in parallel in a second direction orthogonal to the first direction; a beam shape calculation portion that calculates a center of gravity of the particle beam from a first signal output from each of the first linear electrodes and a second signal output from each of the second linear electrodes and that obtains a two-dimensional beam shape of the particle beam around the center of gravity from the first and second signals; a storage portion that accumulates and stores the two-dimensional beam shape corresponding to the center of gravity across a range of the two-dimensional scan; and a display portion that displays the two-dimensional beam shape of the range of the two-dimensional scan stored in the storage portion, as a two-dimensional distribution of a particle beam dose.

To solve the problems, the present invention provides a control method of a particle beam irradiation apparatus comprising a sensor including a plurality of first linear electrodes arranged in parallel in a first direction and a plurality of second linear electrodes arranged in parallel in a second direction orthogonal to the first direction, the control method comprising the steps of: controlling emission of a particle beam; two-dimensionally scanning the particle beam; calculating a center of gravity of the particle beam from a first signal output from each of the first linear electrodes and a second signal output from each of the second linear electrodes; obtaining a two-dimensional beam shape of the particle beam around the center of gravity from the first and second signals; accumulating and storing the two-dimensional beam shapes corresponding to the center of gravity across a range of the two-dimensional scan; and displaying the accumulated and stored two-dimensional beam shapes of the range of the two-dimensional scan, as a two-dimensional distribution of a particle beam dose.

Advantageous Effects of Invention

The particle beam irradiation apparatus and the control method of the particle beam irradiation apparatus according to the present invention can measure and display a dose two-dimensional distribution during scan with a simple configuration, while reducing degradation of a particle beam shape.

DESCRIPTION OF EMBODIMENTS

Embodiments of the present invention will be described with reference to attached drawings.

(1) Configuration and Operation of Conventional Apparatus

Figure 1:
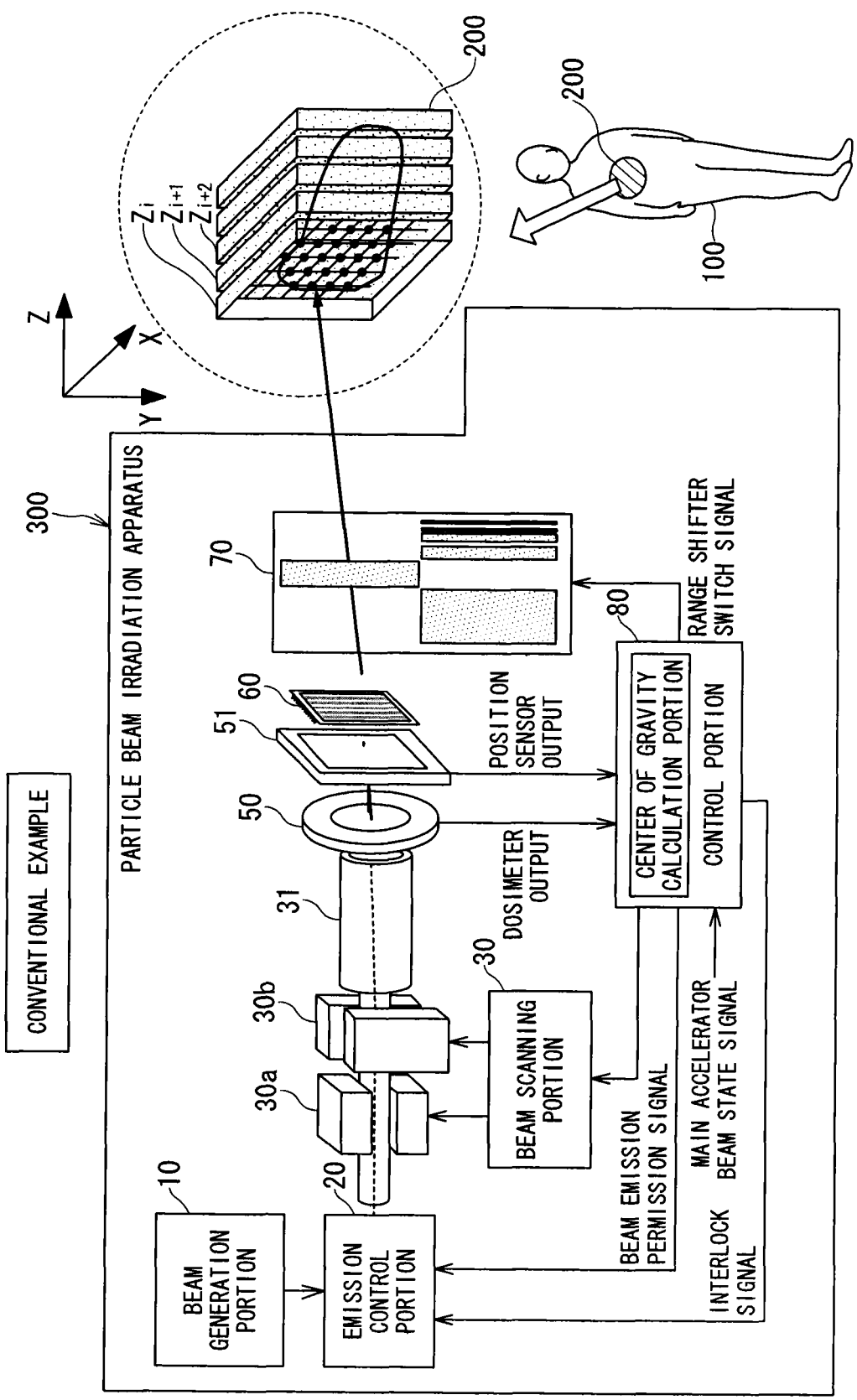
FIG. 1 is a diagram showing an example of configuration of a conventional particle beam irradiation apparatus.

FIG. 1 is a diagram showing an example of configuration of a conventional particle beam irradiation apparatus 300 for comparison with a particle beam irradiation apparatus 1 (FIG. 7) according to the embodiments of the present invention. The particle beam irradiation apparatus 300 includes a beam generation portion 10, an emission control portion 20, a beam scanning portion 30, an X electromagnet 30a, a Y electromagnet 30b, a vacuum duct 31, a dose monitoring portion 50, a position monitoring portion 51, a ridge filter 60, a range shifter 70, a control portion 80, and the like.

The particle beam irradiation apparatus 300 is an apparatus that directs a particle beam, which is obtained by accelerating particles of carbon, protons, or the like to high speed, toward an affected area 200 of a cancer patient 100 to treat cancer. The particle beam irradiation apparatus 300 can carry out three-dimensional scanning irradiation of breaking up the affected area 200 into three-dimensional lattice points and sequentially scanning the lattice points by a particle beam with a small diameter. Specifically, the particle beam irradiation apparatus 300 divides the affected area 200 into plates called slices in an axial direction of the particle beam (Z-axis direction in a coordinate system shown in the upper right of FIG. 1) and sequentially scans two-dimensional lattice points of the divided slices, such as a slice $Z_i$, a slice $Z_{i+1}$, and a slice $Z_{i+2}$ (lattice points in X-axis and Y-axis directions in the coordinate system shown in the upper right of FIG. 1), to thereby perform three-dimensional scanning.

The beam generation portion 10 generates a particle beam by generating particles, such as carbon ions and protons, and using an accelerator (main accelerator), such as a synchrotron, to accelerate the particles up to energy that allows reaching deep in the affected area 200.

The emission control portion 20 controls on/off of emission of the generated particle beam based on a control signal output from the control portion 80.

The beam scanning portion 30 is configured to deflect the particle beam in an X direction and a Y direction and to two-dimensionally scan a slice surface. The beam scanning portion 30 controls exciting currents of the X electromagnet 30a for scan in the X direction and the Y electromagnet 30b for scan in the Y direction.

The range shifter 70 controls a position of the affected area 200 in the Z-axis direction. The range shifter 70 includes, for example, a plurality of acrylic plates in different thicknesses. The acrylic plates can be combined to gradually change energy, i.e. an internal range, of the particle beam passing through the range shifter 70 according to a position of the slice of the affected area 200 in the Z-axis direction. A size of the internal range based on the range shifter 70 is usually controlled to change at an equal distance, and the interval is equivalent to an interval between the lattice points in the Z-axis direction. Examples of a method of switching the internal range include a method of inserting an attenuation object on a path of the particle beam as in the range shifter 70 and a method of changing the energy of the particle beam based on control of an upstream device.

The ridge filter 60 is arranged to spread a sharp peak of a dose in a depth direction inside of the body called a Bragg peak. A spreading width of the Bragg peak based on the ridge filter 60 is set to be equal to the thickness of the slice, i.e. the interval between the lattice points in the Z-axis direction. The ridge filter 60 for three-dimensional scanning irradiation is formed by arranging a plurality of aluminum rod-like members with a substantially isosceles triangle shape in cross section. The peak of the Bragg peak can be spread based on a difference between path lengths generated when the particle beam passes through the isosceles triangles. The spreading width can be set to a desired value based on shapes of the isosceles triangles.

The dose monitoring portion 50 is configured to monitor an irradiated dose. The casing thereof includes: an ionization chamber including parallel electrodes that collect charge generated by ionization of the particle beam; and an SEM (Secondary Electron Monitor) apparatus that measures secondary electrons emitted from a secondary electron emission film arranged in the casing.

The position monitoring portion 51 is configured to identify whether the particle beam scanned by the beam scanning portion 30 is at a correct position. The position monitoring portion 51 includes parallel electrodes for charge collection similar to those of the dose monitoring portion 50. The electrodes for charge collection of the position monitoring portion 51 include linear electrodes (for example, a plurality of strip-shaped electrodes or electrodes made of a plurality of wires) aligned in parallel in the X direction and the Y direction. The plurality of aligned strip electrodes are called strip type electrodes, and the plurality of aligned wire electrodes are called multi-wire type electrodes.

Figure 2:
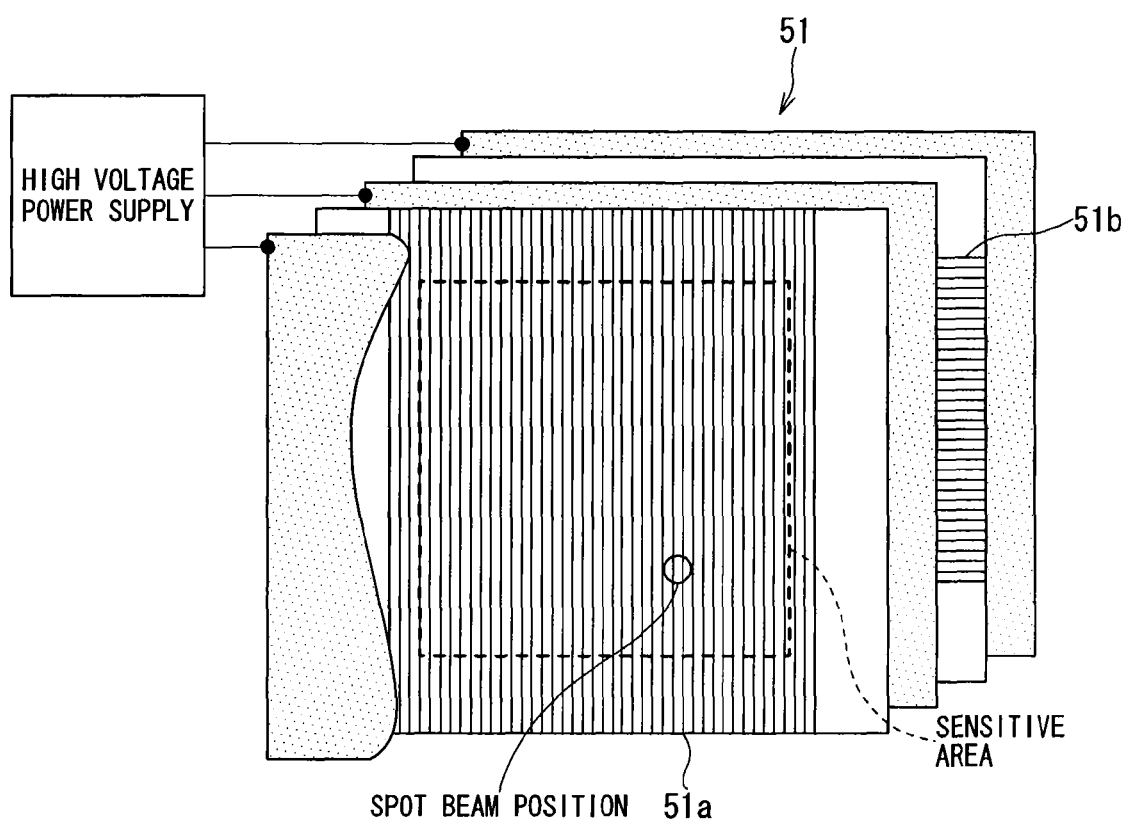
FIG. 2 is a diagram showing an example of configuration of a strip-type position monitoring portion (sensor portion).

FIG. 2 is a diagram showing an example of configuration of the strip-type position monitoring portion 51. As shown in FIG. 2, the position monitoring portion 51 includes a plurality of strip electrodes (a plurality of first linear electrodes) arranged in parallel in an X axial direction (first direction) and a plurality of strip electrodes (a plurality of second linear electrodes) arranged in parallel in a Y axial direction (second direction orthogonal to the first direction).

The control portion 80 is configured to control the entire particle beam irradiation apparatus 1. The control portion 80 controls on/off of the beam emission for the emission control portion 20, issues an instruction related to beam scanning to the beam scanning portion 30, and controls an amount of range shift of the range shifter 70 associated with a slice change.

Figure 3:
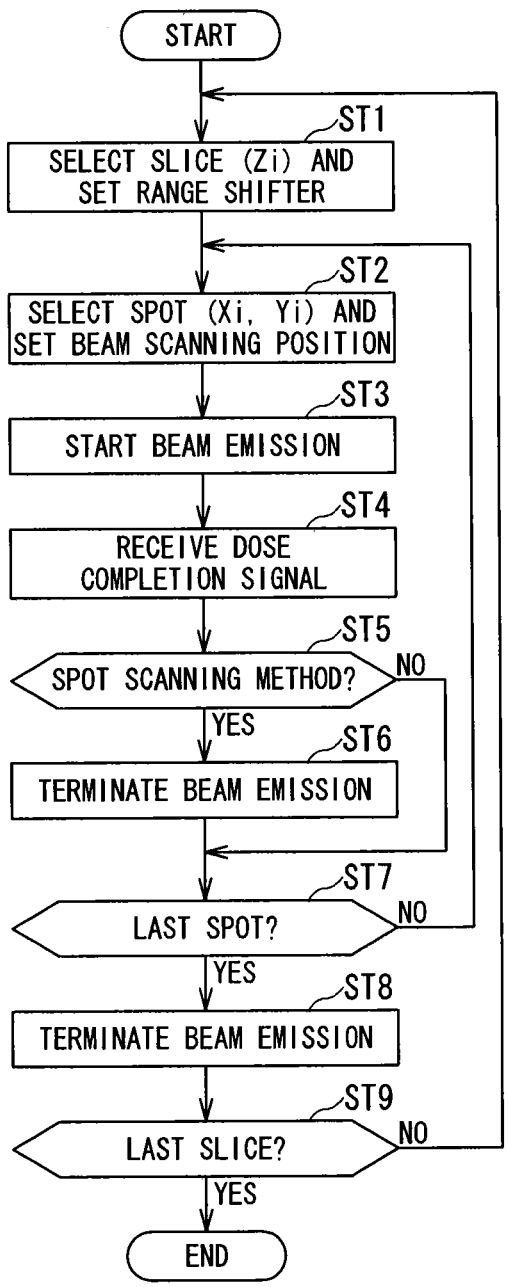
FIG. 3 is a flow chart showing an example of basic processing of three-dimensional scanning irradiation.

FIG. 3 is a flow chart showing an example of basic processing of three-dimensional scanning irradiation.

The affected area is virtually divided into a plurality of slices relative to the beam axis, and one of the divided slices is selected. For example, a slice Zi at a deepest position of the affected area is first selected. Incident energy of the particle beam and a combination of the acrylic plates in the range shifter 70 are selected and set according to the position of the selected slice (step ST1).

The number M of lattice points to be irradiated by the particle beam and a position of a lattice point (Xi, Yi) [i=1 to M], i.e. a spot to be irradiated, are selected according to the shape of the affected area in the deepest slice, and the beam scanning portion 30 sets a direction of the particle beam to the lattice point position (Xi, Yi) (step ST2) on the slice. The emission of the particle beam is started (step ST3).

The ridge filter 60 expands an energy distribution of the particle beam output from the beam scanning portion 30 in the Z-axis direction so that an internal range distribution width corresponds to a slice width.

The dose monitoring portion 50 monitors the irradiation dose for the lattice point (Xi, Yi). When the irradiation dose for the target lattice point reaches a planned dose, a dose completion signal is output to the control portion 80, and the control portion 80 receives the signal (step ST4).

The three-dimensional scanning irradiation is classified into a spot scanning method and a raster scanning method. The spot scanning method is a method of terminating the beam emission when the position of the particle beam is being moved from a lattice point to a next lattice point and restarting the beam emission after the completion of the movement. Therefore, the beam emission is intermittent during the scan of a slice.

On the other hand, in the raster scanning method, the beam emission is continued without being terminated when the position of the particle beam is being moved from a lattice point to a next lattice point. Therefore, the beam emission is continued without being interrupted during the scan of a slice.

In both the spot scanning method and the raster scanning method, the position of the particle beam is terminated until the dose reaches a dose planned in each lattice point, and the position moves to the next lattice point after the dose reaches the planned dose.

In step ST5, whether the method is the spot scanning method or the raster scanning method is determined. If the method is the spot scanning method, the beam emission is temporarily terminated (step ST6), and the beam position is moved to the next spot. The process is repeated up to a last spot of the target slice (step ST7).

On the other hand, if the method is not the spot scanning method, i.e. if the method is the raster scanning method, the beam emission is continued up to the last spot without terminating the beam emission.

When the irradiation of one slice is finished (YES in step ST7), the beam emission is temporarily terminated both in the spot scanning method and the raster scanning method (step ST8), and the process returns to step ST1. A next slice is selected, and setting of the range shifter 70 is changed. The process is repeated up to the last slice (step ST9).

Parameters necessary for the irradiation procedure are described in, for example, a data file called an irradiation pattern file, and the parameters are transferred to the control portion 80 before the start of the therapeutic irradiation. The irradiation pattern file describes, for each lattice point, a range shifter thickness for providing the slice position, drive current values of the X electromagnet 30a and the Y electromagnet 30b for providing the beam position corresponding to the lattice point (X, Y), an irradiation dose for the lattice point, and the like, in the order of irradiation.

Figure 4:
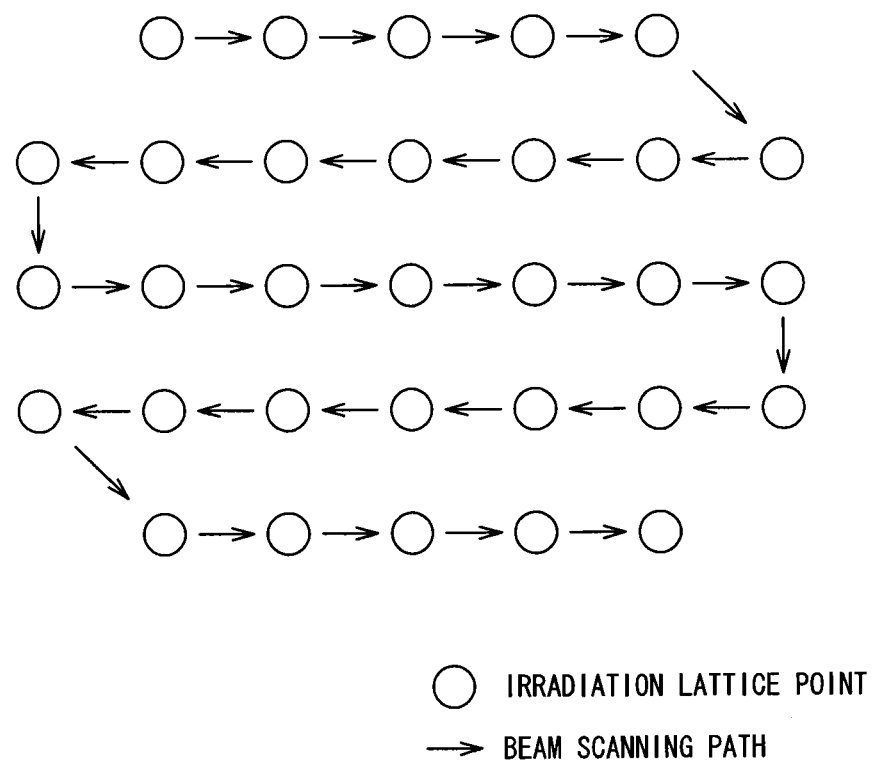
FIG. 4 is a diagram showing an example of a scan pattern on a slice.

FIG. 4 is a diagram showing an example of a scan pattern on a slice. A trajectory pattern from a start lattice point on the upper left to a final lattice point on the lower right is predetermined in the treatment planning, and the particle beam is sequentially scanned in one way along the trajectory pattern.

Figure 5:
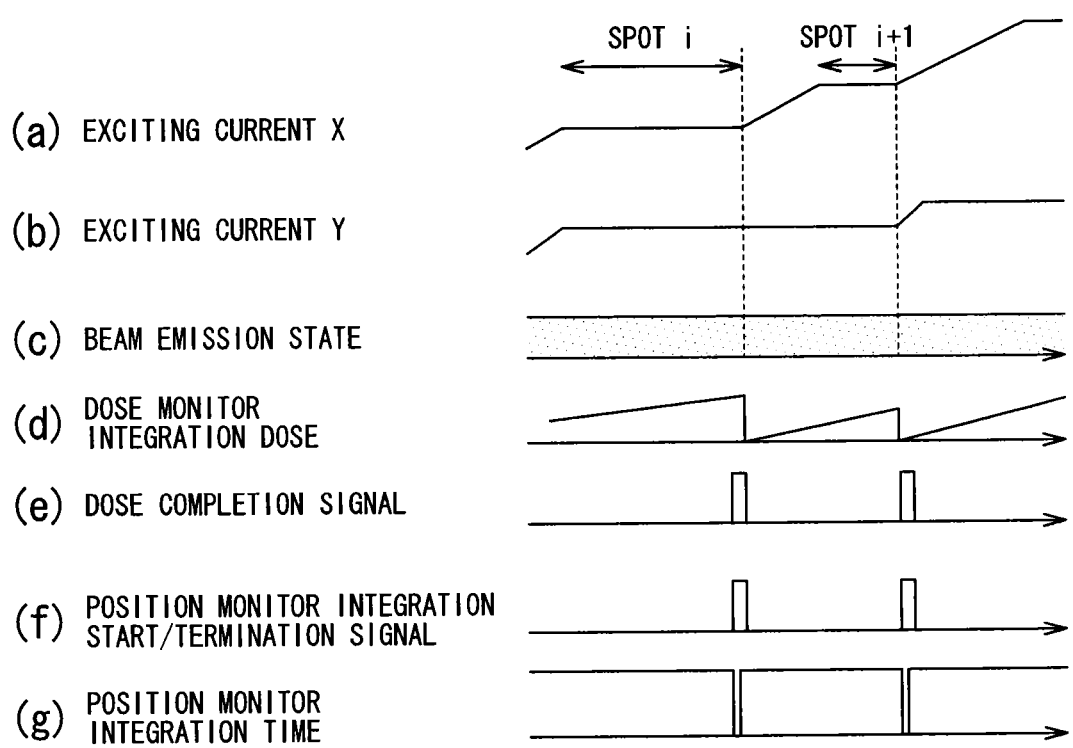
FIG. 5 is a timing chart showing an example of management and control of a dose and a beam position in conventional three-dimensional raster scanning irradiation.

FIG. 5 is a timing chart showing an example of management and control of the dose and the beam position in conventional three-dimensional raster scanning irradiation.

Exciting currents of two electromagnets shown in FIGS. 5(a) and 5(b) correspond to position setting values in two axial directions (X, Y). When the dose measured by the dose monitor (dose monitor integration dose, FIG. 5(c)) reaches a setting value, the dose completion signal (FIG. 5(e)) is output. When the exciting current of the electromagnet reaches the setting value by changing the exciting current, the exciting current value is held. The beam irradiation point moves along with the change in the exciting current of the electromagnet.

As shown in FIGS. 5(f) and 5(g), integration termination, data reading, clearing of integrated charge, and start of integration are continuously performed for each channel of the position monitor based on a signal generated by the dose completion signal in the convention position monitor. The integrated charge can be obtained as a sum of accumulated charge generated during movement of irradiation points and accumulated charge generated by the beam directed to the termination irradiation points.

Figure 6:
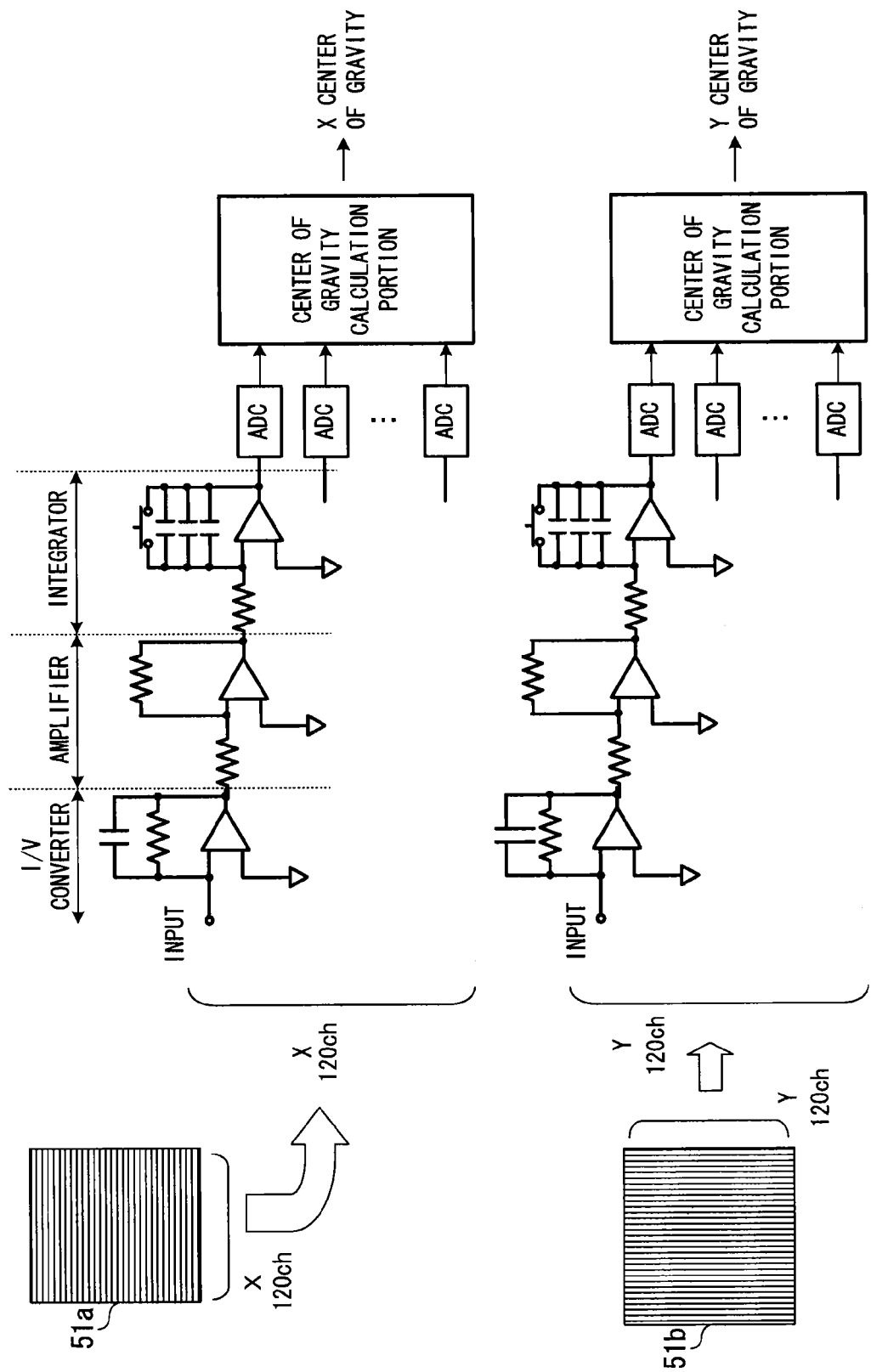
FIG. 6 is a diagram showing an example of a conventional position monitor (position monitoring portion and beam position detection circuit).

FIG. 6 is a diagram showing an example of the conventional position monitor (the position monitoring portion 51 and a beam position detection circuit). In the conventional beam position detection circuit, an I/V converter that converts a current output to a voltage signal, an amplifier that amplifies the voltage signal, an integrator connected to the amplifier, and an ADC circuit for A/D conversion are connected in each channel of the accumulated electrodes. Three capacitors are connected to the integrator to secure the accuracy for the irradiation points in relation to a difference of two digits in the irradiation time, and the capacitors can be switched to change an integration time constant.

In the beam position detection circuit, a center of gravity calculation portion configured an FPGA (Field Programmable Gate Array) and the like is arranged on each of the two accumulated electrodes 51a and 51b. The center of gravity calculation portion imports the output of the ADC circuit and calculates the center of gravity to calculate the center of gravity (Xc, Yc) for each of the two accumulated electrodes 51a and 51b.

The calculated center of gravity (Xc, Yc) is compared with a predetermined position setting value (Xr, Yr). If a difference between the values (Xc−Xr or Yc−Yr) exceeds a tolerance, it is determined that the position is abnormal. The interlock signal is generated, and the beam emission is terminated.

In this way, the conventional position monitor has a function of calculating the center of gravity of the beam to determine whether the position of the spot beam is normal.

However, information obtained from the conventional position monitor is information just discretely showing an estimated center of gravity of each beam spot. A continuous dose distribution formed as a superposition of spot positions cannot be obtained.

Meanwhile, doctors and technicians desire to visually check the dose profiles during irradiation (two-dimensional distribution of the dose in the X and Y directions or one-dimensional distribution of the dose in the X and Y directions cut out from the two-dimensional distribution). For example, if the dose profiles are displayed slice by slice, the accuracy of irradiation can be checked for the treatment, and secure treatment is possible.

Consequently, the particle beam irradiation apparatus 1 according to the present embodiments provides a method of highly accurate monitoring of continuous dose profiles with a simple configuration.

(2) Particle Beam Irradiation Apparatus According to the Present Embodiments (First Embodiment)

Figure 7:
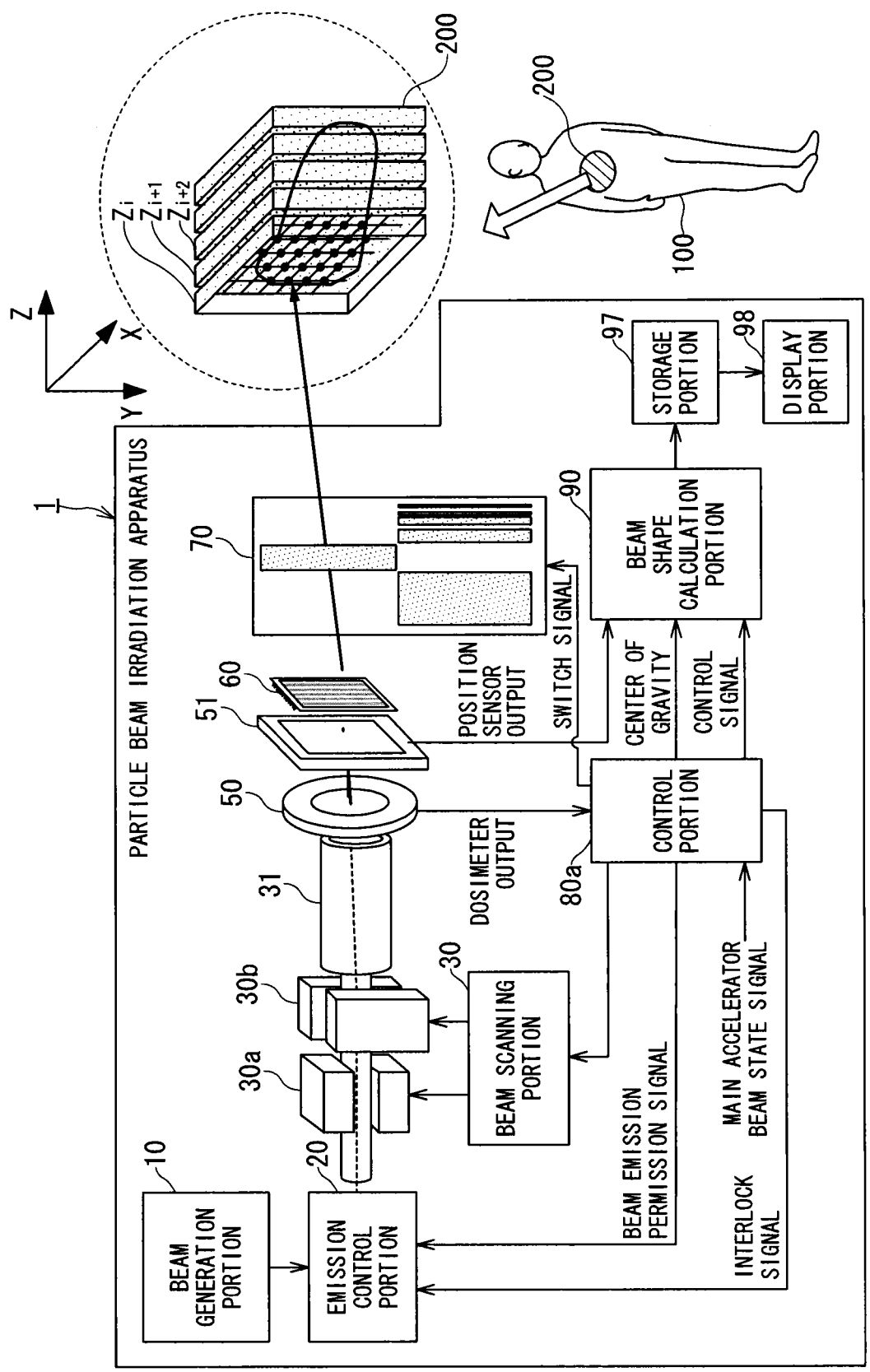
FIG. 7 is a diagram showing an example of configuration of a particle beam irradiation apparatus according to a first embodiment.

FIG. 7 is a diagram showing an example of configuration of the particle beam irradiation apparatus 1 according to a first embodiment. The particle beam irradiation apparatus 1 according to the first embodiment includes a beam shape calculation portion 90, a storage portion 97, and a display portion 98 in addition to the configuration of the conventional particle beam irradiation apparatus 300.

The particle beam irradiation apparatus 1 according to the first embodiment includes the same position monitoring portion 51 as in the conventional technique. However, while the conventional position monitoring portion 51 is used as a sensor for abnormality determination of the beam position, the position monitoring portion 51 in the first embodiment is used as a sensor for obtaining dose profiles.

The beam shape calculation portion 90 calculates the center of gravity of the particle beam from X channel signals (first signals) output from the X electrodes 51a (first linear electrodes) of the position monitoring portion 51 (sensor portion) and from Y channel signals (second signals) output from the Y electrodes 51b (second linear electrodes). The beam shape calculation portion 90 obtains two-dimensional beam shapes of the particle beam around the center of gravity from a plurality of X channel signals and Y channel signals.

The storage portion 97 accumulates and stores the two-dimensional beam shapes corresponding to the center of gravity, across the range of the two-dimensional scan. The display portion 98 displays, the two-dimensional shapes of the two-dimensional scan range stored in the storage portion 97, as a two-dimensional distribution of the particle beam dose.

Figure 8:
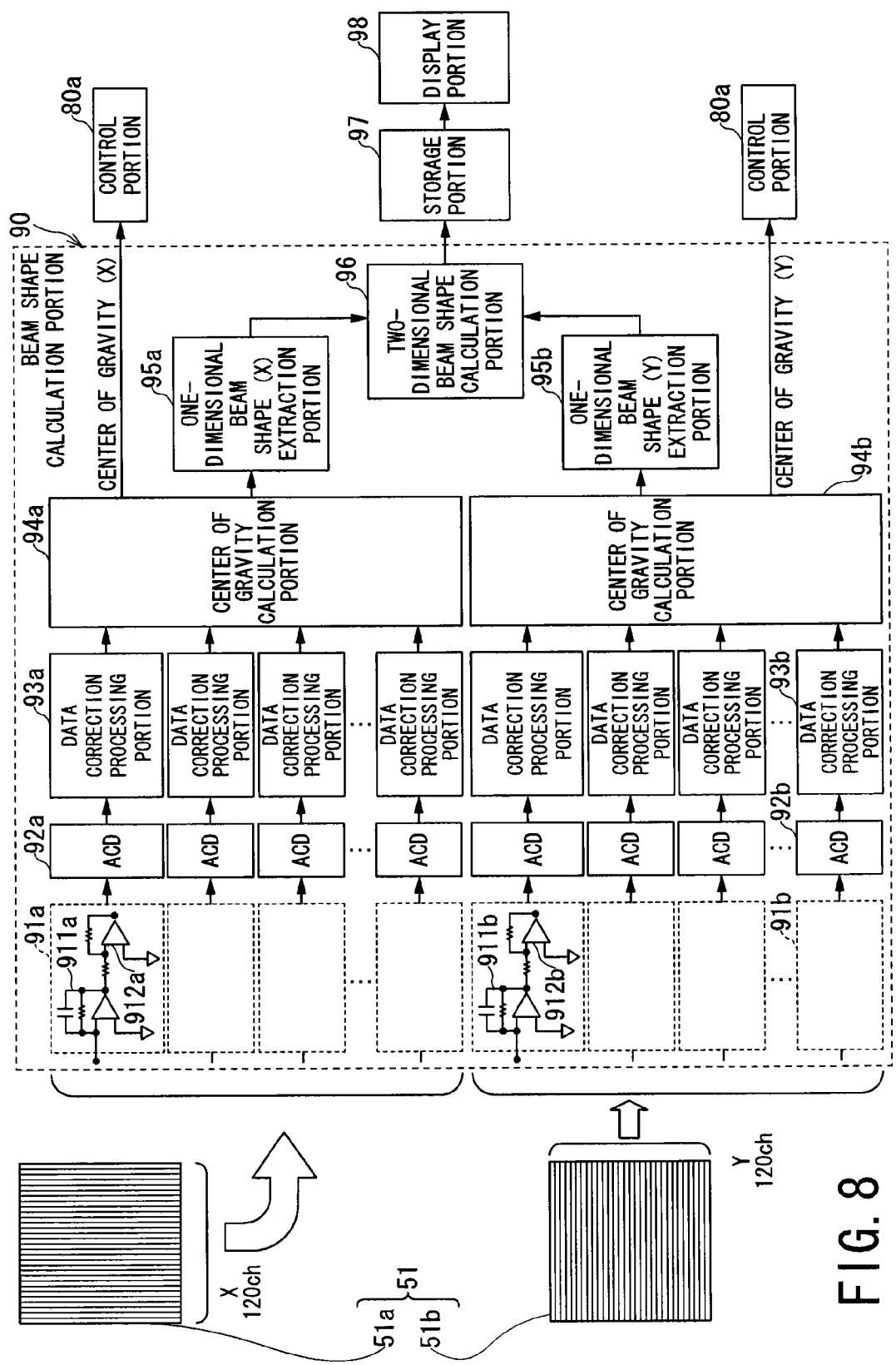
FIG. 8 is a block diagram showing a detailed example of configuration of a beam shape calculation portion (first embodiment).

FIG. 8 is a block diagram showing a detailed example of configuration of the beam shape calculation portion 90.

Although the numbers of the X electrodes 51a and the Y electrodes 51b (the numbers of channels) of the position monitoring portion 51 are not particularly limited, an example in which the numbers of channels in the X and Y directions are both 120 channels will be described below.

A current voltage conversion (IV conversion) circuit 911a converts an output current of the X electrode 51a to a voltage. An amplifier 912a amplifies the voltage to an appropriate voltage, and an AD converter (ADC) 92a converts the voltage to a digital signal. A data correction processing portion 93a of a next stage applies an offset correction process and a smoothing process to the digital signal and outputs the digital signal to a center of gravity calculation portion 94a.

The IV conversion circuit 911a, the amplifier 912b, the ADC 92a, and the data correction processing portion 93a are arranged on each of the X electrodes 51a, and the components are arranged for 120 channels in the example.

Similarly, IV conversion circuits 911b, amplifiers 912b, ADCs 92b, and data correction processing portions 93b of 120 channels are arranged on the Y electrodes 51a.

Center of gravity calculation portions 94a and 94b of a next stage calculate the center of gravity in the X direction and the center of gravity in the Y direction of the particle beam, respectively, from amplitude values of the channel signals in the X and Y directions applied with the offset correction process and the smoothing process. A method of calculating the center of gravity is not particularly limited, and a conventional known technique can be used.

A one-dimensional beam shape (X) extraction portion 95a obtains a one-dimensional beam shape (first beam shape) in the X direction (first direction) from the amplitude values of a plurality of X channel signals (first signals) around the calculated center of gravity in the X direction. A one-dimensional beam shape (Y) extraction portion 95b similarly obtains a one-dimensional beam shape in the Y direction.

Figure 9:
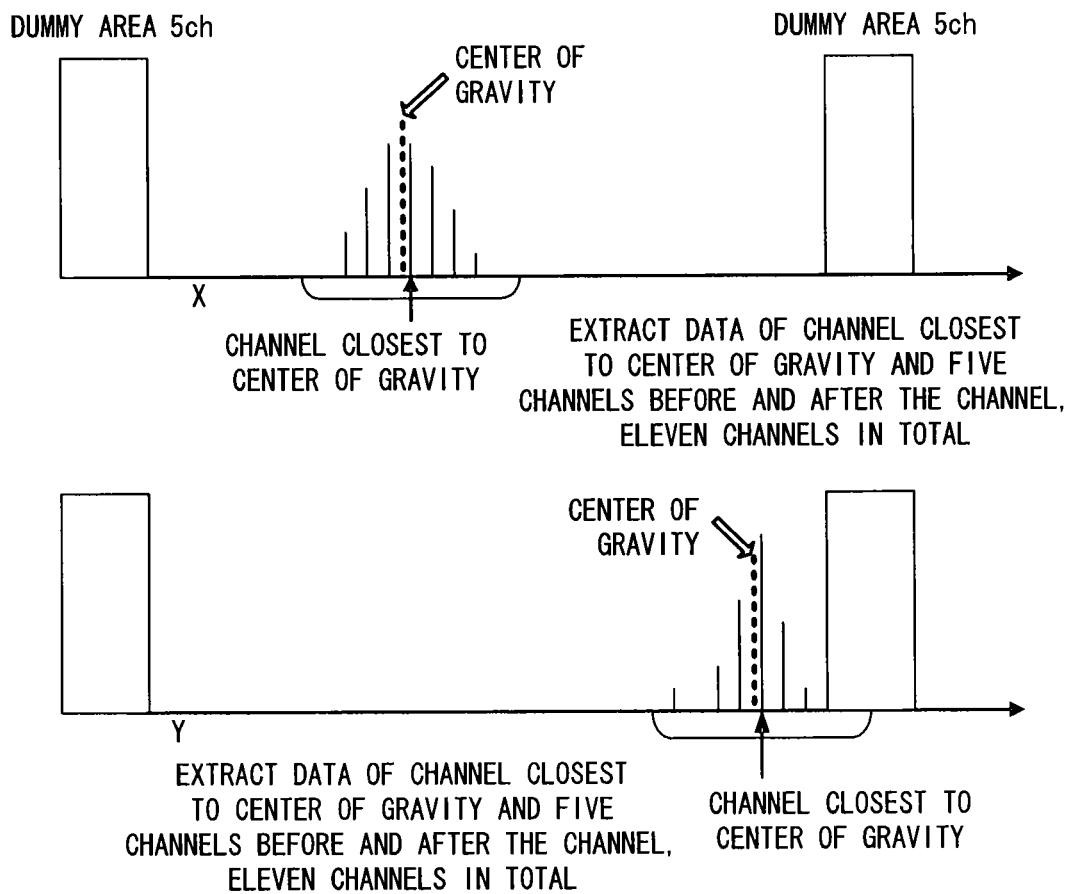
FIG. 9 is a diagram showing a concept of a process of obtaining a one-dimensional beam shape from each channel signal.

FIG. 9 is a diagram showing a concept of the process of obtaining the one-dimensional beam shape from the channel signals. When the center of gravity in the X direction is obtained, a channel closest to the center of gravity (the channel will be called a "center channel Ncx") is specified from 120 channels in the X direction. An amplitude value X (Ncx) of a signal of the center channel and amplitude values of signals of n channels, for example, five channels, before and after the center channel are extracted. If the extracted amplitude values of the signals of n+1 channels are written as, for example, $Xi=X(i)$; (i=Ncx−n to Ncx+n: i and n are integers), the one-dimensional beam shape in the X direction can be expressed by a data sequence F(Xi) including the extracted amplitude values of the signals of n+1 channels arranged in order of the channels.

Similarly, if an amplitude value Y (Ncy) of a signal of a channel closest to the center of gravity in the Y direction (center channel Ncy) and amplitude values of signals of m channels before and after the center channel (for example, five channels before and after the center channel) are written as, for example, $Yj=Y(j)$; (j=Ncy−m to Ncy+m; j and m are integers), the one-dimensional beam shape in the Y direction can be expressed by a data sequence F(Yj) including the extracted amplitude values of the signals of m+1 channels arranged in order of the channels.

A two-dimensional beam shape calculation portion 96 obtains a two-dimensional beam shape G(Xi, Yj) as in a following formula from a product of the obtained one-dimensional beam shapes F(Xi) and F(Yj) in the X and Y directions.

$$G(Xi, Yj)=F(Xi)\cdot F(Yj) \qquad \text{(Formula 1)}$$

$Xi=X(i)$; (i=Ncx−n to Ncx+n: i and n are integers)
$Yj=Y(j)$; (j=Ncy−m to Ncy+m: j and m are integers)

The larger the numbers of channels m and n forming the two-dimensional beam shape G(Xi, Yj) (i.e. the numbers of channels extracted from all channels), the higher the accuracy of the beam shape. However, an increase in the numbers of channels more than necessary just leads to increases in operation time and data transfer time. Appropriate numbers of channels are mostly determined by a beam size (beam width) and intervals between the linear electrodes.

The beam shape can be schematically approximated by a Gaussian distribution shape, and in this case, the beam size can be approximated by a standard deviation of the Gaussian distribution. If the beam size (standard deviation) is 5 mm, the range for forming the beam profile is about 20 mm around the center of gravity. Therefore, if the channel intervals (intervals between the linear electrodes) are 2 mm, an appropriate range for transmission is eleven channels around the channel closest to the center of gravity (the center channel and five channels before and after the center of gravity).

In this way, the appropriate numbers of channels forming the two-dimensional beam shape G(Xi, Yj) vary depending on the beam size. Therefore, it is preferable that the numbers of channels extracted from all channels can be changed.

Figure 10:
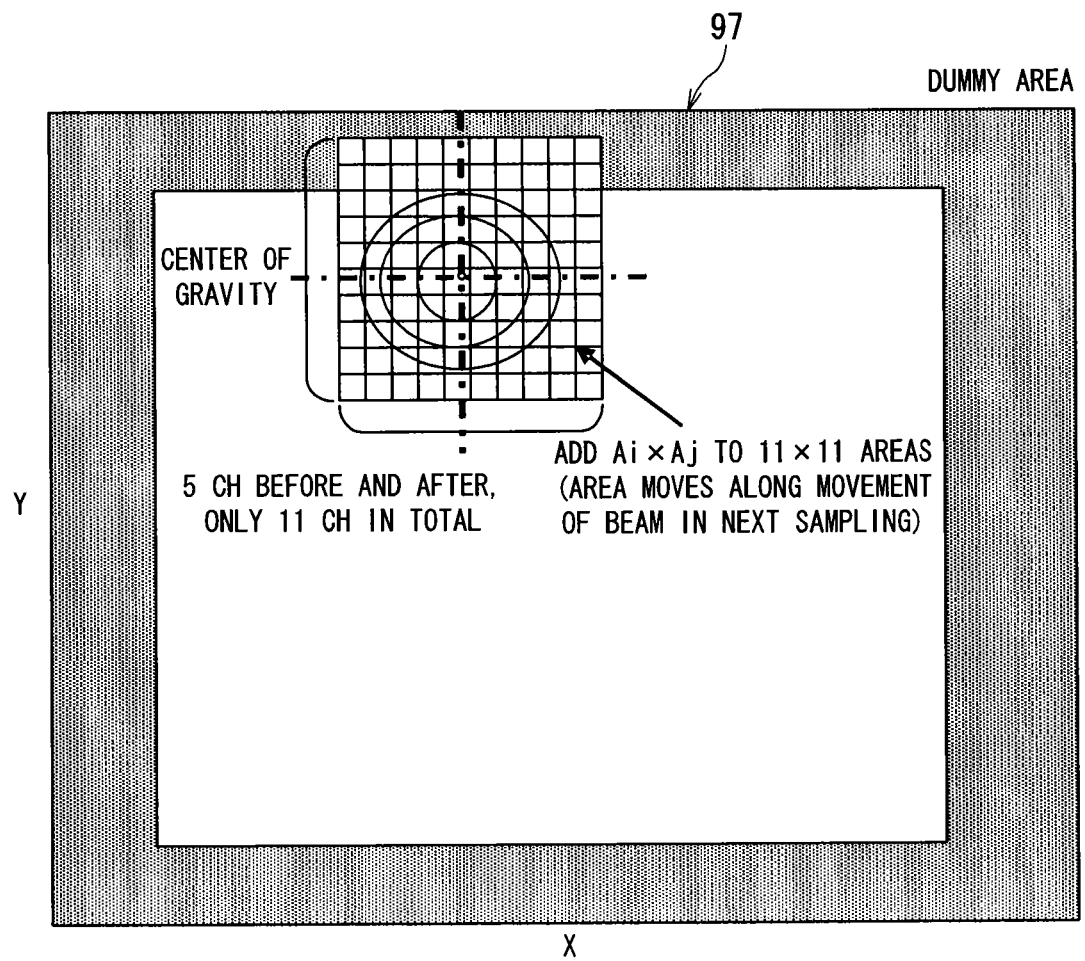
FIG. 10 is a diagram two-dimensionally expressing a storage area of a storage portion.

The two-dimensional beam shape G(Xi, Yj) calculated by the formula is transferred to the storage portion 97. FIG. 10 is a diagram two-dimensionally expressing a storage area of the storage portion 97. FIG. 10 illustrates a state of storing the two-dimensional beam shape G(Xi, Yj) in addresses corresponding to the channel number i in the X direction and the channel number j in the Y direction. As described, the numbers of all channels in the X and Y directions are 120 each in the example, and the numbers of all channels in the X and Y directions forming the two-dimensional beam shape G(Xi, Yj) are eleven each.

Irregular data values enter if the center of gravity is within five channels from ends (minimum channel 1 or maximum channel 120) of the image area. To prevent this, X and Y can have areas (dummy areas) with a value 0 in five channels outside of 120 channels as shown in FIG. 10.

Figure 11:
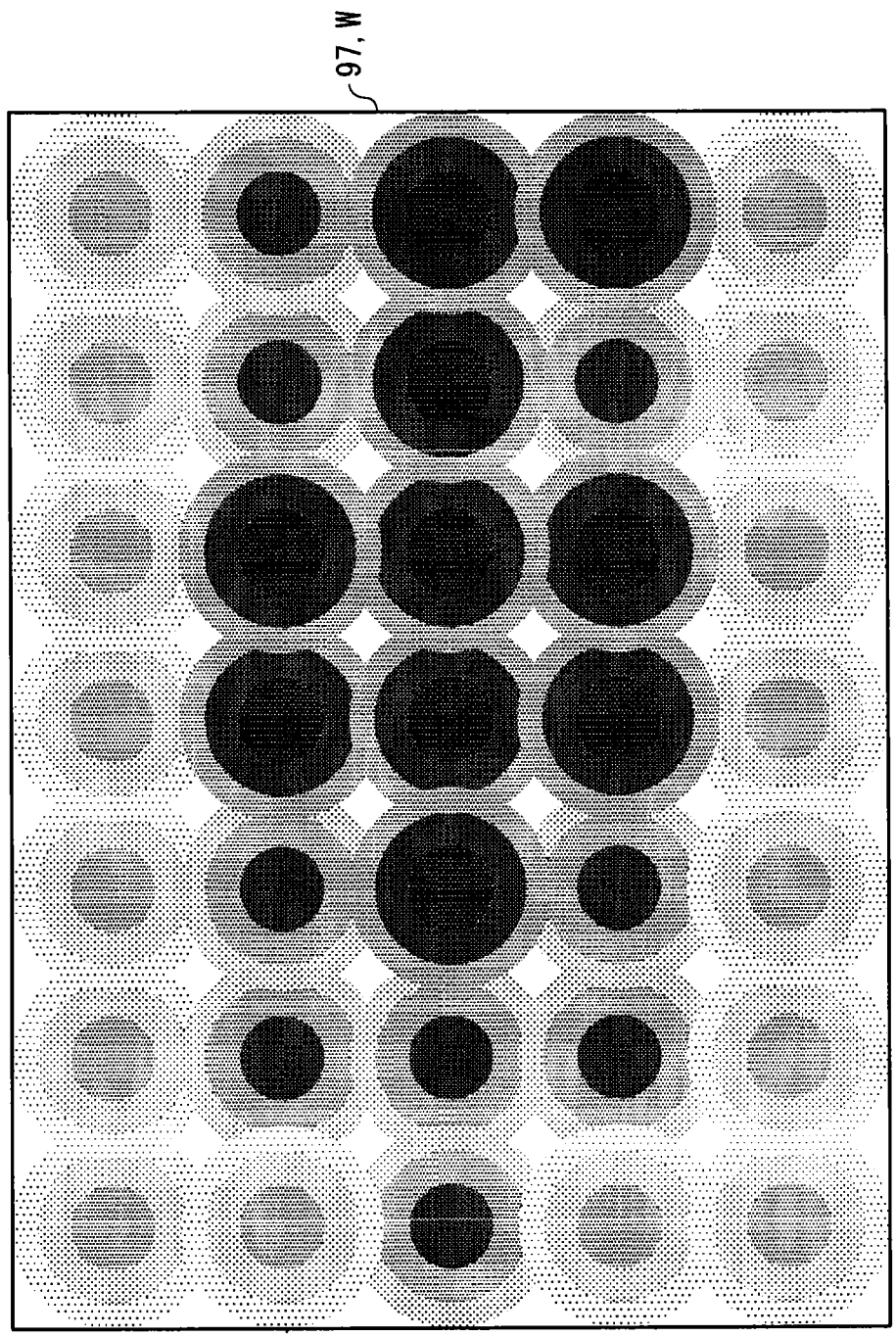
FIG. 11 is a diagram showing a display concept of dose profiles (two-dimensional distribution of dose) across an entire range of a two-dimensional scan range of slices.

If the set current value of the scanning electromagnet is changed by the spot switch, the spot position changes accordingly, and similar profile data is formed near different centers of gravity. The profile data can be accumulated and stored in the storage portion 97 to obtain dose profiles (two-dimensional distribution of the dose) across the entire range of the two-dimensional scan range of the slices as illustrated in FIG. 11.

The dose profiles accumulated and stored in the storage portion 97 are transmitted to the display portion 98, for example, slice by slice. The dose profiles are displayed on a screen W of the display portion 98 corresponding to the storage area of the storage portion 97, and the dose profiles can be easily viewed.

Figure 12:
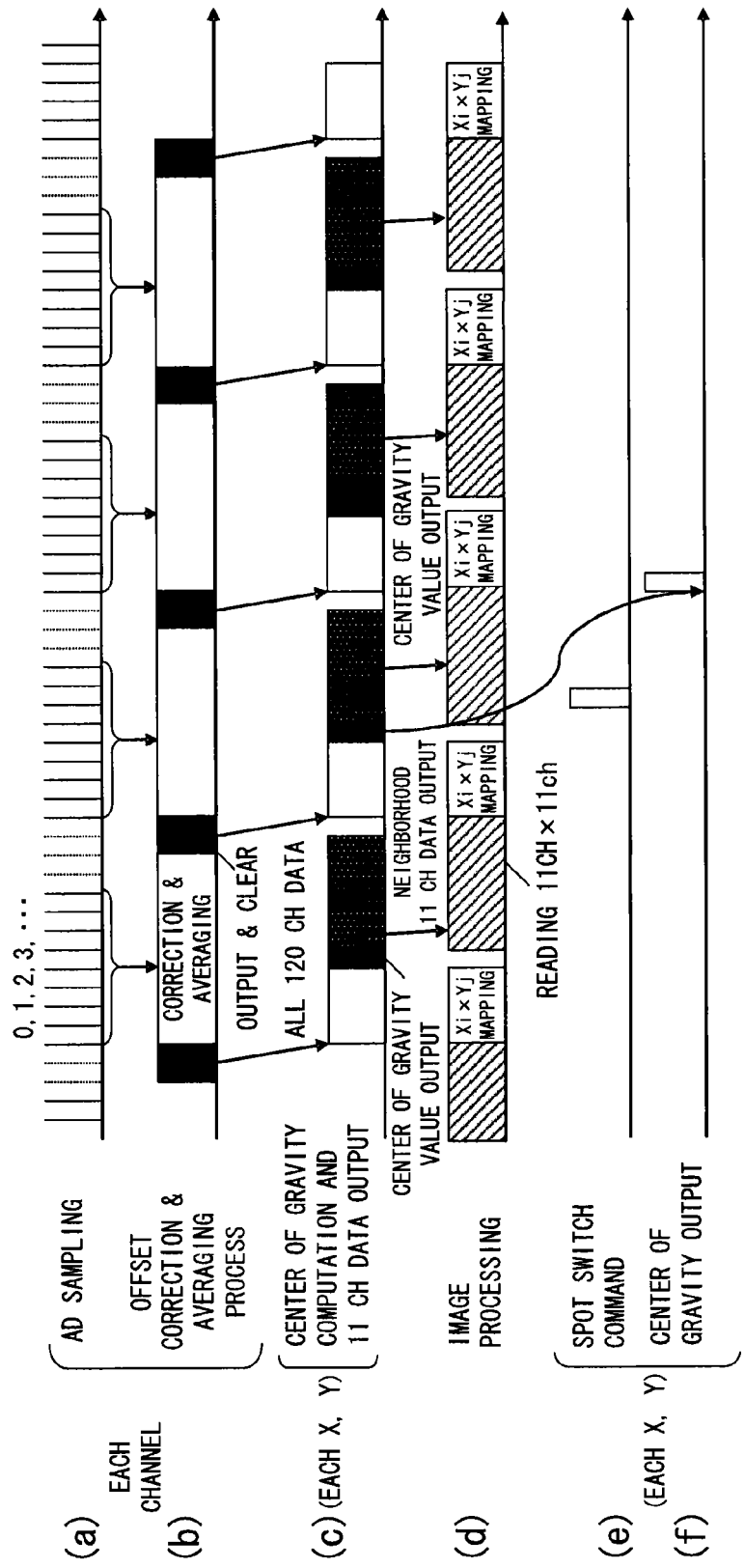
FIG. 12 is a timing chart of processes by a beam shape calculation portion and processing of storing the dose profiles in the storage portion.

FIG. 12 is a timing chart of processes by the beam shape calculation portion 90 and a process of storing the dose profiles in the storage portion 97.

The AD converters 92a arranged for the channels sample channel signals of all channels in parallel, for example, every 0.2 µs and apply AD conversion to the channel signals (FIG. 12(*a*)). The data correction processing portions 93a correct offsets of the channels for the output signals of the AD converters 92a and further execute an averaging process to reduce influence of noise. The channel signals in the X direction applied with the average process are transmitted to the center of gravity calculation portions 94a for X, for example, every 5 µs. The channel signals in the Y direction applied with the average process are similarly transmitted to the center of gravity calculation portions 94b for Y (FIG. 12(*b*)).

The center of gravity calculation portions 94a and 94b for X and Y use the input data of 120 channels in the X and Y directions to perform center of gravity computation in the X and Y directions to obtain the center of gravity. The one-dimensional beam shape (X) extraction portion 95a and the one-dimensional beam shape (Y) extraction portion 95b extract the channel data of eleven channels near the center of gravity. The calculation of the center of gravity and the extraction of the data of eleven channels near the center of gravity are performed at, for example, a 5 µs period in synchronization with the input of the data (FIG. 12(*c*)).

The extracted data of eleven channels in each of the X and Y directions (one-dimensional beam shapes F(Xi) and F(Yj)) is output to the two-dimensional beam shape calculation portion 96. The two-dimensional beam shape calculation portion 96 performs the computation of Formula 1 and transmits the calculated two-dimensional beam shape G(Xi, Yj) to the storage portion 97. The storage portion 97 sequentially accumulates and stores the transmitted two-dimensional beam shapes G(Xi, Yj) in corresponding channels.

The process of calculating the two-dimensional beam shape and the process of storing the two-dimensional beam shape in the storage portion 97 (image processing shown in FIG. 12(*d*)) are also executed at, for example, a 5 µs period in synchronization with the input of the data.

When a slice switch command is received from the control portion 80a, the storage portion 97 outputs the accumulated and stored two-dimensional beam shapes, i.e. the dose profiles, to the display portion 98 to display the slice-by-slice dose profiles on the display portion 98.

Meanwhile, when a spot switch signal is received from the control portion 80a (FIG. 12(*e*)), the center of gravity in the X and Y directions calculated by the center of gravity calculation portions 94a and 94b is transmitted to the control portion 80a (FIG. 12(*f*)), and the control portion 80a determines abnormal/normal of the beam position as in the conventional technique.

The conventional particle beam irradiation apparatus only has a function of using the channel signals output from the position monitoring portion 51 to calculate the center of gravity of the particle beam to perform abnormality determination of the beam position.

On the other hand, in addition to the function of calculating the center of gravity of the particle beam to perform the abnormality determination of the beam position, the particle beam irradiation apparatus 1 according to the first embodiment can use the channel signals output from the position monitoring portion 51 to generate the dose profiles to display the dose profiles on the display portion 98 as a two-dimensional image. As a result of the display of the dose profiles, the doctors and the radiological technicians can visually check during irradiation whether the dose two-dimensional distribution during scan is a correct distribution. The output signals from the position monitoring portion 51 included in the conventional apparatus can be processed to generate the dose profiles, without separately arranging a special apparatus called a multi-array profile monitor on the beam path. Therefore, a same sharp beam shape as in the conventional particle beam irradiation apparatus can be maintained without increasing the beam size (beam width) caused by insertion of the multi-array profile monitor.

The dose profiles are generated for the output signals from the position monitoring portion 51 that exists conventionally, by a relatively simple process. Therefore, an increase in the cost of the entire apparatus can be reduced.

(3) Second Embodiment

Figure 13:
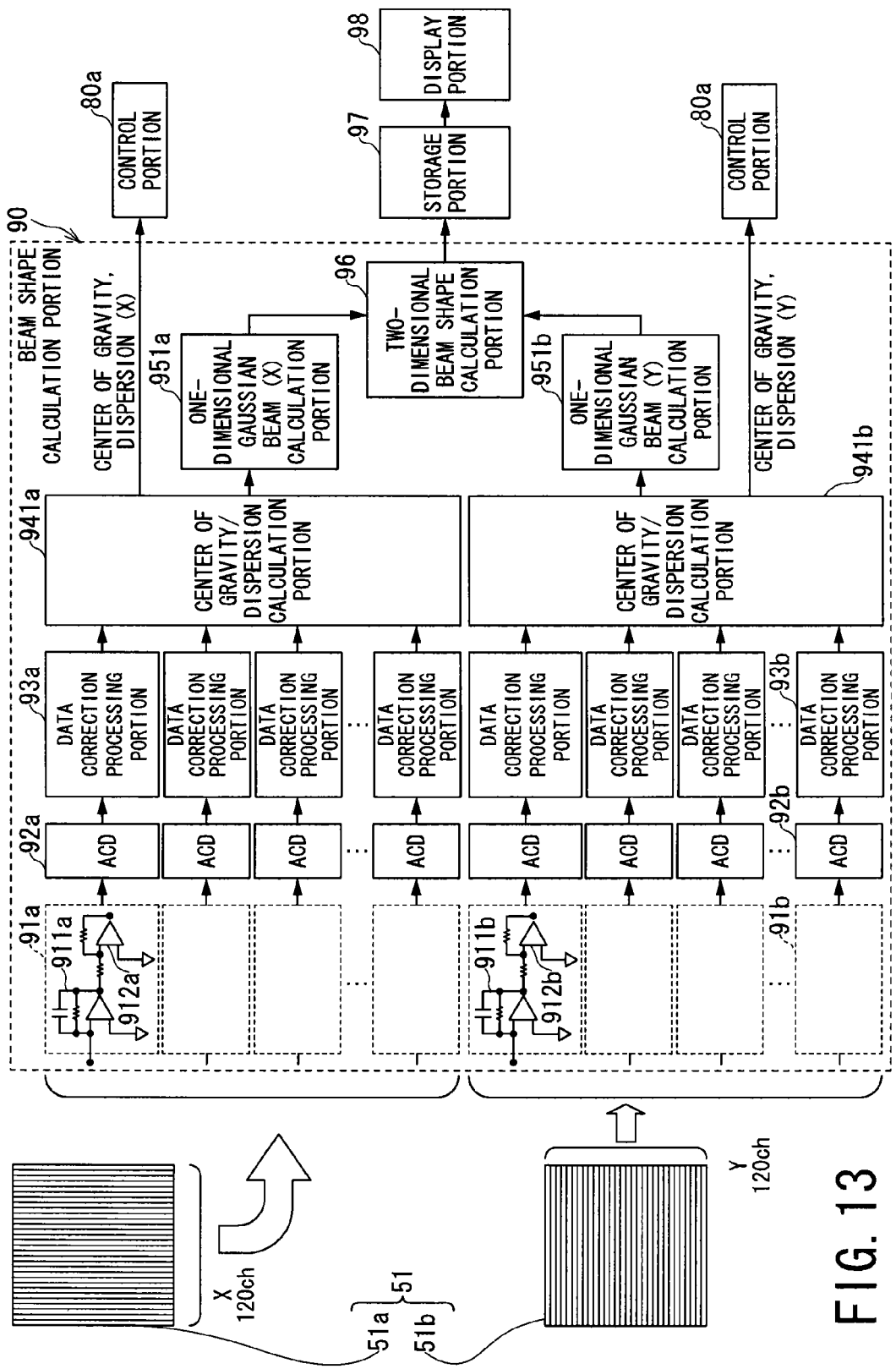
FIG. 13 is a block diagram showing a detailed example of configuration of the beam shape calculation portion (second embodiment).

A second embodiment according to the present invention will be described. FIG. 13 is a diagram showing an example of configuration of the beam shape calculation portion 90a of the particle beam irradiation apparatus 1 according to the second embodiment. Configurations with the same functions as in the first embodiment are designated with the same reference numerals as in FIG. 8.

In the second embodiment, after the data correction processing portions 93a and 93b perform the offset correction and the smoothing process for each channel, center of gravity/dispersion calculation portions 941a and 941b calculate a center of gravity (X', Y') in the X and Y directions and calculate a dispersion (Sx, Sy) of positions X and Y.

The center of gravity (X') and the dispersion (Sx) in the X direction are calculated by, for example, following formulas. In the formulas, x denotes channel numbers (x: 1 to 120), P(x) denotes channel signals of the channels, and A denotes a sum of the channel signals.

[Math. 1]

$$A = \sum_{x=1}^{n} P(x) \quad \text{(Formula 2)}$$

[Math. 2]

$$X' = \frac{1}{A} \cdot \sum_{x=1}^{n} x \cdot P(x) \quad \text{(Formula 3)}$$

[Math. 3]

$$Sx = \frac{1}{A} \cdot \sum_{x=1}^{n} [x^2 \cdot P(x)] - X'^2 = \frac{1}{A} \sum_{x=1}^{n} [(x - X')^2 \cdot P(x)] \quad \text{(Formula 4)}$$

Meanwhile, a one-dimensional Gaussian beam calculation portion 951a assumes that an X direction one-dimensional beam shape can be approximated by a Gaussian beam shape and uses the calculated center of gravity (X') and dispersion (Sx) to calculate an X direction one-dimensional beam shape F(x, Sx) by a following formula.

[Math. 4]

$$F(x, Sx) = \frac{1}{\sqrt{2\pi Sx}} \cdot \exp\left[-\frac{1}{2} \cdot \frac{(x - X')^2}{Sx}\right] \quad \text{(Formula 5)}$$

Similarly, a one-dimensional Gaussian beam calculation portion 951b uses the calculated center of gravity (Y') and dispersion (Sy) to calculate a Y direction one-dimensional beam shape F(y, Sy) by a following formula.

[Math. 5]

$$F(y, Sy) = \frac{1}{\sqrt{2\pi Sy}} \cdot \exp\left[-\frac{1}{2} \cdot \frac{(y - Y')^2}{Sy}\right] \quad \text{(Formula 6)}$$

As in the first embodiment, the two-dimensional beam shape calculation portion 96 calculates a product of two one-dimensional beam shapes (both are one-dimensional Gaussian beam shapes in the second embodiment) to calculate a two-dimensional beam shape G(x, y) as in a following formula.

$$G(x, y) = F(x, Sx) \cdot F(y, Sy) \quad \text{(Formula 7)}$$

The one-dimensional Gaussian beam calculation portions 951a and 951b store the center of gravity and the dispersion in an appropriate memory every time the center of gravity and the dispersion are transmitted. When a slice switch signal is received, the one-dimensional Gaussian beam calculation portions 951a and 951b perform the computations of Formulas 5 and 6, and the two-dimensional beam shape calculation portion 96 performs the computation of Formula 7 to create a dose profile. The dose profiles are accumulated and stored in the storage portion 97. When the dose profiles of one slice are accumulated, the dose profiles are output to the display portion 98 to display the dose profiles.

Although the dose profiles can be created and displayed in both the first and second embodiments, the first and second embodiments have following differences.

In the first embodiment, the process of creating the one-dimensional beam shape and the two-dimensional beam shape and the process of accumulating and storing the shapes in the storage portion 97 are executed in parallel, every time the center of gravity is calculated. Therefore, the dose profiles can be immediately displayed when the slice switch command is received. Raw data is used to calculate the two-dimensional data, without approximating the beam shape by a specific distribution shape (Gaussian distribution shape in the example) as in the second embodiment. Therefore, a degree of coincidence with an actual two-dimensional distribution is high.

On the other hand, the process of creating the one-dimensional beam shape and the two-dimensional beam shape is executed after the reception of the slice switch command in the second embodiment. Therefore, although it takes time to output the image data, a memory for storing the image data is not necessary in the signal processing circuit. Therefore, the second embodiment is suitable when the number of channels in the position monitor is large. The storage of the calculated dispersion facilitates tracing of a cause when an abnormality is found in the image. This is because a square root of the dispersion is a standard deviation, which serves as an index directly indicating the beam size.

As described, the particle beam irradiation apparatus 1 and the control method of the particle beam irradiation apparatus 1 according to the first and second embodiments can measure and display the dose two-dimensional distribution (dose profiles) during scan with a simple configuration, while reducing degradation in the particle beam shape.

The present invention is not limited to the embodiments, and the present invention can be embodied by modifying the constituent elements in an execution phase without departing from the concept of the present invention. Various inventions can be formed based on appropriate combinations of a plurality of constituent elements disclosed in the embodiments. For example, some constituent elements among all constituent elements illustrated in the embodiments may be deleted. Constituent elements across different embodiments may also be appropriately combined.

| | Description of Symbols |
|---|---|
| 1 | particle beam irradiation apparatus |
| 10 | beam generation portion |
| 20 | emission control portion |
| 30 | beam scanning portion |
| 51 | position monitoring portion (sensor portion) |
| 90 | beam shape calculation portion |
| 97 | storage portion |
| 98 | display portion |

The invention claimed is:

1. A particle beam irradiation apparatus comprising:
a beam generation portion that generates a particle beam;
a beam emission control portion that controls emission of the particle beam;
a beam scanning portion that two-dimensionally scans the particle beam;
a sensor portion including a plurality of first linear electrodes arranged in parallel in a first direction and a plurality of second linear electrodes arranged in parallel in a second direction orthogonal to the first direction;
a beam shape calculation portion that calculates a center of gravity of the particle beam from a first signal output from each of the first linear electrodes and a second signal output from each of the second linear electrodes and that obtains a two-dimensional beam shape of the particle beam around the center of gravity from the first and second signals;
a storage portion that accumulates and stores the two-dimensional beam shapes corresponding to the center of gravity across a range of the two-dimensional scan; and
a display portion that displays the two-dimensional beam shapes of the range of the two-dimensional scan stored in the storage portion, as a two-dimensional distribution of a particle beam dose.

2. The particle beam irradiation apparatus according to claim 1, wherein
the beam shape calculation portion
obtains the two-dimensional beam shapes from amplitude values of a plurality of the first and second signals around the center of gravity.

3. The particle beam irradiation apparatus according to claim 2, wherein
the beam shape calculation portion
obtains a first beam shape on an axis in the first direction and a second beam shape on an axis in the second direction from the amplitude values of the plurality of first and second signals around the center of gravity and obtains a beam shape in an area other than the two axes based on a product of the first beam shape and the second beam shape to obtain the two-dimensional beam shape.

4. The particle beam irradiation apparatus according to claim 1, wherein
the beam shape calculation portion
obtains a dispersion of a position from amplitude values of a plurality of the first and second signals around the center of gravity and sets a Gaussian distribution shape determined by the center of gravity and the dispersion as the two-dimensional beam shape.

5. The particle beam irradiation apparatus according to claim 4, wherein
the beam shape calculation portion
obtains a first dispersion at a position in the first direction and a second dispersion at a position in the second direction from the amplitude values of the plurality of first and second signals around the center of gravity,
sets s first beam shape on an axis in the first direction as a first Gaussian distribution shape determined by the center of gravity and the first dispersion, sets a second beam shape on an axis in the second direction as a second Gaussian distribution shape determined by the center of gravity and the second dispersion, and
obtains a beam shape of an area other than the two axes based on a product of the first beam shape and the second beam shape to obtain the two-dimensional beam shape.

6. The particle beam irradiation apparatus according to claim 1, wherein
the beam scanning portion
two-dimensionally scans slices by the particle beam, the slices obtained by dividing an affected area to be irradiated in an axial direction of the particle beam,
the storage portion
accumulates and stores, slice by slice, the two-dimensional beam shapes across a range of the two-dimensional scan, and
the display portion
displays, slice by slice, the two-dimensional beam shapes as a two-dimensional distribution of a particle beam dose.

7. A control method of a particle beam irradiation apparatus comprising a sensor including a plurality of first linear electrodes arranged in parallel in a first direction and a plurality of second linear electrodes arranged in parallel in a second direction orthogonal to the first direction, the control method comprising the steps of:
controlling emission of a particle beam;
two-dimensionally scanning the particle beam;
calculating a center of gravity of the particle beam from a first signal output from each of the first linear electrodes and a second signal output from each of the second linear electrodes;
obtaining a two-dimensional beam shape of the particle beam around the center of gravity from the first and second signals;
accumulating and storing the two-dimensional beam shapes corresponding to the center of gravity across a range of the two-dimensional scan; and
displaying the accumulated and stored two-dimensional beam shapes of the range of the two-dimensional scan, as a two-dimensional distribution of a particle beam dose.

8. The control method of the particle beam irradiation apparatus according to claim 7, wherein
in the step of obtaining the two-dimensional beam shape,
the two-dimensional beam shape is obtained from amplitude values of a plurality of the first and second signals around the center of gravity.

9. The control method of the particle beam irradiation apparatus according to claim 8, wherein
in the step of obtaining the two-dimensional beam shape,
a first beam shape on an axis in the first direction and a second beam shape on an axis in the second direction are obtained from the amplitude values of the plurality of first and second signals around the center of gravity, and a beam shape in an area other than the two axes is obtained based on a product of the first beam shape and the second beam shape to obtain the two-dimensional beam shape.

10. The control method of the particle beam irradiation apparatus according to claim 7, wherein
in the step of obtaining the two-dimensional beam shape,
a dispersion of a position is obtained from amplitude values of a plurality of the first and second signals around the center of gravity, and a Gaussian distribution shape determined by the center of gravity and the dispersion is set as the two-dimensional beam shape.

11. The control method of the particle beam irradiation apparatus according to claim 10, wherein
in the step of obtaining the two-dimensional beam shape,
a first dispersion at a position in the first direction and a second dispersion at a position in the second direction are obtained from the amplitude values of the plurality of the first and second signals around the center of gravity,
a first beam shape on an axis in the first direction is set as a first Gaussian distribution shape determined by the center of gravity and the first dispersion, a second beam shape on an axis in the second direction is set as a second Gaussian distribution shape determined by the center of gravity and the second dispersion, and
a beam shape of an area other than the two axes is obtained based on a product of the first beam shape and the second beam shape to obtain the two-dimensional beam shape.

12. The control method of the particle beam irradiation apparatus according to claim 7, wherein
in the step of two-dimensionally scanning,
slices are two-dimensionally scanned by the particle beam, the slices obtained by dividing an affected area to be irradiated in an axial direction of the particle beam,
in the step of accumulating and storing,
the two-dimensional beam shapes are accumulated and stored, slice by slice, across a range of the two-dimensional scan, and
in the step of displaying,
the two-dimensional beam shapes are displayed, slice by slice, as a two-dimensional distribution of a particle beam dose.

* * * * *